United States Patent
Grady et al.

(10) Patent No.: US 8,190,449 B2
(45) Date of Patent: May 29, 2012

(54) ALERT DISTRIBUTION AND MANAGEMENT SYSTEM AND RETURNS MODULE

(75) Inventors: Patrick Charles Grady, Woodbridge, VA (US); Richard Hardy Fiddleman, Bethesda, MD (US); Robert Irwin Patt-Corner, Cabin John, MD (US)

(73) Assignee: Noblis, Inc., Falls Church, VA (US)

( * ) Notice: Subject to any disclaimer, the term of this patent is extended or adjusted under 35 U.S.C. 154(b) by 359 days.

(21) Appl. No.: 12/071,101

(22) Filed: Feb. 15, 2008

(65) Prior Publication Data

US 2008/0262948 A1 Oct. 23, 2008

Related U.S. Application Data

(60) Provisional application No. 60/901,659, filed on Feb. 16, 2007.

(51) Int. Cl.
- *G06Q 10/00* (2012.01)
- *G06G 1/14* (2006.01)
- *G06Q 20/00* (2012.01)
- *G07B 17/00* (2006.01)
- *G07F 19/00* (2006.01)

(52) U.S. Cl. .................... 705/2; 705/22; 705/28; 705/30

(58) Field of Classification Search ............... 705/22, 705/28, 2, 30
See application file for complete search history.

(56) References Cited

U.S. PATENT DOCUMENTS

| | | | | |
|---|---|---|---|---|
| 6,115,690 A | * | 9/2000 | Wong | 705/7.27 |
| 2001/0056359 A1 | * | 12/2001 | Abreu | 705/3 |
| 2002/0111822 A1 | | 8/2002 | Shimizu et al. | |
| 2002/0156797 A1 | * | 10/2002 | Lee et al. | 707/200 |
| 2003/0093328 A1 | | 5/2003 | Koons | |
| 2004/0143518 A1 | | 7/2004 | Siegel | |
| 2004/0267608 A1 | | 12/2004 | Mansfield, Jr. | |
| 2005/0038691 A1 | | 2/2005 | Babu | |
| 2005/0273369 A1 | * | 12/2005 | Ota et al. | 705/4 |
| 2005/0283259 A1 | | 12/2005 | Wolpow | |
| 2006/0161392 A1 | * | 7/2006 | Sholl et al. | 702/183 |
| 2009/0144104 A1 | * | 6/2009 | Johnson | 705/7 |

OTHER PUBLICATIONS

International Search Report for PCT/US 07/23965 (mailed Nov. 25, 2008) (3 pages).
Written Opinion of the International Searching Authority for PCT/US 07/23965 (mailed Nov. 25, 2008) (4 pages).
Product Recall Services—Stericycle—Manufacturer Recall Services, etc., http://www.stericycle.com/product_recall_services.html, printed Aug. 26, 2008.

(Continued)

*Primary Examiner* — Ig T An
(74) *Attorney, Agent, or Firm* — Finnegan, Henderson, Farabow, Garrett & Dunner, L.L.P.

(57) ABSTRACT

A method for managing a returns process in response to product alerts is provided. The method includes receiving an alert related to a product. The method also includes processing the alert into an alert repository. The method further includes retrieving product data based on the alert. The method further includes associating the product data with the alert. The method further includes facilitating a return of the product to a vendor using the product data. The method further includes receiving data in response to the return of the product. The method further includes providing an actionable display including the product data, the data in response to the return, and data related to a return action.

20 Claims, 14 Drawing Sheets

OTHER PUBLICATIONS

International Search Report for PCT/US2008/001996 (mailed Oct. 22, 2008) (3 pages).
Written Opinion of the International Searching Authority for PCT/US2008/001996 (mailed Oct. 22, 2008) (8 pages).
Copending U.S. Appl. No. 11/984,280; Titled: Alert Distribution and Management System and Interface Components; filed Nov. 15, 2007 (49 pages).
Office Action mailed on Apr. 6, 2010, in co-pending U.S. Appl. No. 11/984,280, (14 pages).
International Preliminary Report on Patentability, mailed May 27, 2010, in PCT Application No. PCT/US2007/023965 (6 pages).
Final Office Action mailed on Sep. 24, 2010, in co-pending U.S. Appl. No. 11/984,280, (9 pages).
Office Action mailed on Dec. 23, 2010, in co-pending U.S. Appl. No. 12/358,399, (11 pages).
Office Action dated May 13, 2011 in co-pending U.S. Appl. No. 11/984,280, 9 pages.
Office Action dated Jun. 8, 2011 in co-pending U.S. Appl. No. 12/385,399, 12 pages.
Jewler, "Reducing Patient Safety Risks Through Innovations in Managing Recalls," *Horizons Perspectives in Healthcare Management and Information Technology*, Fall, 2006, pp. 30-36.
"Management of Product and Device Alerts/Recalls and Other Related Hazards," *Mitretek Systems*, www.mitretek.org, pp. 1-5.
"RASMAS Data Collection Workbook Instructions," Jan. 25, 2007, 7 pages.
"RASMAS Overview—Revolutionizing Product Recall Management," *Mitretek Systems*, http://rasmas.mitretek.org, 13 pages.
"Risk and Safety Management Alert System—Implementation Guide," *Mitretek Systems*, http://rasmas.mitretek.org, 45 pages.

\* cited by examiner

RASMAS
RISK AND SAFETY MANAGEMENT ALERT SYSTEM

HOME & MY PROFILE · HELP · CONTACT · LOGOUT

COORDINATE ALERTS

RESPOND | COORDINATE | CLOSED ALERTS | ALL ALERTS

THIS LIST CONTAINS 5 ALERTS.

SHOW ONLY: [ALL ▼]  SORT ALERTS BY: [ALERT ID ▼] (GO)

SEARCH: [  ] (GO)

UPLOAD CLOSE
NEW ALERT CHECKED

| ALERT ID (RELEASE DATE) | ALERT TYPE | DOMAIN | DESCRIPTION/MANUFACTURER/REASON | DISTRIBUTION | ALERT STAGE | ALERT STATUS | SELECT FOR CLOSE |
|---|---|---|---|---|---|---|---|
| 2007050271 (5/16/2007 18:41 EDT) | RECALL | BLOOD PRODUCTS | RED BLOOD CELLS<br>AMERICAN NATIONAL RED CROSS, PENN.-JERSEY REGION, PHILADELPHIA, PA, BLOOD PRODUCTS, COLLECTED FROM AN UNSUITABLE DONOR DUE TO A HISTORY OF HEMOCHROMATOSIS, WERE DISTRIBUTED. | NJ | NO ASSIGNMENTS | ESCALATED | ☐ |
| 2007050260 (5/16/2007 18:41 EDT) | RECALL | BLOOD PRODUCTS | PLATELETS, PHERESIS, LEUKOCYTES REDUCED<br>AMERICAN NATIONAL RED CROSS, PACIFIC NORTHWEST REGION, PORTLAND, OR BLOOD PRODUCTS, WHICH WERE MISLABELED AS TO HLA TYPE, WERE DISTRIBUTED. | ID, OR, AND WA | NO ASSIGNMENTS | ESCALATED | ☐ |
| 2007050258 (5/16/2007 18:41 EDT) | RECALL | BLOOD PRODUCTS | RED BLOOD CELLS AND FRESH FROZEN PLASMA<br>AMERICAN NATIONAL RED CROSS, PACIFIC NORTHWEST REGION, PORTLAND, OR BLOOD PRODUCTS, WHICH TESTED NEGATIVE FOR HEPATITIS B SURFACE ANTIGEN (HBsAg) AND FOR THE ANTIBODY TO HEPATITIS B CORE ANTIGEN (anti-HBc), BUT WERE COLLECTED FROM A DONOR WHO PREVIOUSLY TESTED POSITIVE FOR HBsAg, WERE DISTRIBUTED. | OR AND CA | NO ASSIGNMENTS | ESCALATED | ☐ |
| 2007050253 (5/16/2007 12:58 EDT) | RECALL | BLOOD PRODUCTS | RED BLOOD CELLS, LEUKOCYTES REDUCED<br>AMERICAN NATIONAL RED CROSS, NORTHEASTERN PENNSYLVANIA REGION, ASHLEY, PA. BLOOD PRODUCTS, WHICH DID NOT MEET THE QUALITY CONTROL REQUIREMENTS FOR DISTRIBUTION, WERE DISTRIBUTED | OK AND MD | NO ASSIGNMENTS | ESCALATED | ☐ |
| 2007050245 (5/16/2007 12:58 EDT) | RECALL | BLOOD PRODUCTS | RED BLOOD CELLS AND FRESH FROZEN PLASMA<br>UNITED BLOOD SERVICES, MERIDIAN, MS BLOOD PRODUCTS, COLLECTED FROM DONORS WHO MAY HAVE RECEIVED INAPPROPRIATE ARM PREPARATION, WERE DISTRIBUTED. | AL, MS, AND UK | NO ASSIGNMENTS | ESCALATED | ☐ |

RASMAS
RISK AND SAFETY MANAGEMENT ALERT SYSTEM

⌂ HOME & MY PROFILE ⓘ HELP ✉ CONTACT ⊠ LOGOUT

Return Details

ALERT #2005020056

Description: Noblis 2 Dual Channel Syringe Infusion Pump, Noblis 1 Single Channel Syringe Infusion Pump and Noblis 2 Syringe Pump

Manufacturer: Noblis Clinical Technology, Natick, MA

Reason: Potential pump motor/encoder assembly failure may cause over medication in patients

Domain: Biomedical Devices

- Edit Product Keys
- Add Advice Record
- Add Return Record
- Add Shipping Record
- Add Financial Record
- Alert Details

VIEW RETURN DETAILS FOR ALERT #2005020056

PRODUCT INFORMATION (3 PRODUCTS)    ☐ HIDE DETAILS

| Product Key | Product Description | Model/Product Number | Stock Identifiers | Volume | Recall ID |
|---|---|---|---|---|---|
| Noblis 2 Dual | (a) Noblis 2 Dual Channel Syringe Infusion Pump | P/N 20001-001 | (a) Serial number range: 2080002251 - 408203175 | 1,334 | Z-0431-06 ☐ |
| Item 2 | (b) Noblis 1 Single Channel Syringe Infusion Pump | P/N 2003-001 | (b) Serial number range: 308102012 - 408102213 | 1,334 | Z-0432-05 ☐ |
| Noblis 2 | (c) Noblis 2 Syringe Pump | P/N 2005-001 | (c) Serial number range 21800222 - 2180002382; 02R00222 - 02R002382; 318002383 - 318002426 | 1,334 | Z-0433-05 ☐ |

Make your sort and filter selections by using the boxes below, then click on the Go button

Choose one or more facilities:
Krial Commonwealth Care Center
Krial Emergency Care Center of Reston
Krial Fair Oaks Hospital

Choose on ore more products
All Records
No Product Key
Noblis 2 Dual
Noblis 1 Single

Select by date:
Create Date Descending
(Go)

| ADVICE | RETURNS | PROCUREMENT | FINANCIAL | SUMMARY |

KRIAL EMERGENCY CARE CENTER OF RESTON

| Product Key: | Noblis 2 Dual |
|---|---|
| Note: | PO 69908796 indicates that we purchased 4 of these in December 2004. Return activity advice record #1227-a, revision 1. Last updated Lynda Spar 02/08/2005. |
| Local Description: | HVD-PMP2 Infusion Dual |
| Stock Identifiers: | 208002865, 34655667, 40250036, 24279845 |
| Facility Stock ID: | HVD PMP 3555, HVD PMP Blue Labels |
| Locations: | Check storage closets on Levels B and D |
| Volume & Unit Type | 4 Pumps |
| Purchase Order: | HVD-69908796 |
| Vender ID / Name: | 778336777 / Device Management LTD |

Edit | Delete | Add Advice Record | Add Return Record | Add Shipment Record | Add Financial Record |

EDIT PRODUCT KEY

KRIAL EMERGENCY CARE CENTER OF RESTON

| Product Key | Noblis 2 |

RASMAS
RISK AND SAFETY MANAGEMENT ALERT SYSTEM

⌂HOME  ⛨MY PROFILE  ⓘHELP  ✉CONTACT  ⎆LOGOUT

Add Financial Record

ALERT #2005020056

ADD FINANCIAL RECORD FOR ALERT #2005020056
Click on button in the Original Product information section to choose the product you want to associate to this return record.
Choosing the top button associates the return record with the entire alert.

Description:
Noblis 2 Dual Channel Syringe Infusion Pump, Noblis 1 Single Channel Syringe Infusion Pump and Noblis 2 Syringe Pump

Manufacturer:
Noblis Clinical Technology, Natick, MA

Reason:
Potential pump motor/encoder assembly failure may cause over medication in patients

Domain:
Biomedical Devices
■ Return Details
■ Alert Details

ORIGINAL PRODUCT INFORMATION     ☐ HIDE DETAILS

| Product Key | Product Description | Model/Product Number | Stock Identifiers | Volume | Recall ID | |
|---|---|---|---|---|---|---|
| Noblis 2 Dual | (a) Noblis 2 Dual Channel Syringe Infusion Pump | P/N 20001-001 | (a) Serial number range: 2080002251 - 408203175 | 1,334 | Z-0431-06 | ▪ |
| Item 2 | (b) Noblis 1 Single Channel Syringe Infusion Pump | P/N 2003-001 | (b) Serial number range: 308102012 - 408102213 | 1,334 | Z-0432-05 | ▪ |
| Noblis 2 | (c) Noblis 2 Syringe Pump | P/N 2005-001 | (c) Serial number range 21800222 - 21800002382; 02R00222 - 02R002382; 318002383 - 318002426 | 1,334 | Z-0433-05 | ▪ |

FINANCIAL RECORD INFORMATION

| Product Key | Local Product Description | Local Model/Product Number |
|---|---|---|
| Entire Alert: | | |

Note:

| Credit Taken | Credit Number | Financial Activity Type |
|---|---|---|

Facilities
☐ Krial Commonwealth Care Center
☐ Krial Emergency Care Center of Reston
☐ Krial Fair Oaks Hospital

ADDITIONAL INFORMATION      ☐ SHOW DETAILS ( OKAY )          ( CANCEL )

(12) United States Patent
US 8,190,449 B2

ALERT DISTRIBUTION AND MANAGEMENT SYSTEM AND RETURNS MODULE

RELATED APPLICATIONS

This application claims the benefit of the filing date of U.S. Provisional Application No. 60/901,659 filed Feb. 16, 2007, incorporated in its entirety herein by reference.

FIELD OF THE INVENTION

The present invention relates generally to an enterprise application. More particularly, the present invention relates to managing a returns process of recalled products in an alert distribution and management system.

BACKGROUND OF THE INVENTION

When a manufacturer determines that a product is defective, the manufacturer may issue an alert (e.g., a recall notice, field correction, repair instructions, etc.) to notify customers to stop using the product, return the product, etc. Issuing an alert is costly to a manufacturer because an alerted product may need to be replaced or fully refunded, but it often limits liability for a manufacturer and prevents further damage to the manufacturer's corporate image. A product alert is not, however, easy to learn about because, for example, a manufacturer may not always publicize an alert. A manufacturer may merely notify a government agency, and it is often a consumer group that publicizes an alert that the group learns from the agency. Further, a customer may have hundreds or thousands of products to search for alerts on.

The current process used by many organizations to obtain and manage product alerts (e.g., product recalls and bulletins) is thus seriously flawed. There may be multiple alert sources and formats and diverse methods of alert distribution to the organizations. The process may rely on poorly functioning paper-based systems. Critical alerts may often be mishandled or lost. Weeks may pass before recalled products may be discarded. Timely information regarding the status of the alerts may not be available.

The problems with the business process of alert management fall into three general areas: organization, infrastructure, and process. Organizationally, alert management may often be performed by individual departments in an organization. For example, a hospital may expect each department (medical devices, food service, pharmacy, etc.) to process recalls for relevant products. There may be no overall coordination and responsibility for alert management and no assurance that all departments are covered. The infrastructure may tend to consist of manual mechanisms, such as receiving recall notices by mail. The manual mechanism may not support efficient workflow or timely, comprehensive reporting. The process may be fragmented and inconsistent across the organization. Determining accountability may often be difficult, and there may not be an easy way to ensure appropriate actions have been taken. Many recalls may be missed or may be implemented too slowly.

The problems also extend to the process of returning recalled products and receiving refunds, reimbursements, and/or replacements from the vendor for the recalls. There may be no infrastructure or process for associating recalls with purchase or inventory data of recalled products that are currently in stock, and associating recalls with refunds, reimbursements, and/or replacements that are due from the vendor. Thus, it has been difficult to efficiently manage a returns process of recalled products and track whether refunds, reimbursements, and/or replacements have been received for a particular recalled product or recall.

SUMMARY OF THE INVENTION

An alert distribution and management system with a returns module using information technology may alleviate the alert and returns management problems. One example of an alert distribution and management system may be the Risk and Safety Management Alert System (RASMAS™) with a returns module from Noblis. The alert distribution and management system with the returns module may provide organizations with a new infrastructure for alert and returns management.

In an alert distribution and management system with a returns module consistent with embodiments of the present invention, alerts may be managed within an enterprise-wide organization including a management structure and responsibilities. Management may assure that the full range of relevant product domains (e.g., departments or categories of products) may be addressed. The alert distribution and management system may also have an automated infrastructure to support effective workflow and provide immediate and comprehensive reporting. An alert distribution and management system may include a repository containing a full history of actions taken in response to an alert, and the repository may enable audits and reviews of the actions. The process may be comprehensive and standardized across the organization. Management may monitor adherence to the process and to the organizational standards, and accountability may be well-defined.

In addition, in an alert distribution and management system with a returns module consistent with embodiments of the present invention, data about recalled products, such as purchase history and inventory data, may be collected and associated with alerts, enabling a user to view and manage a returns process. Financial data related to refunds, reimbursements, and replacements may also be collected and associated with alerts, allowing a user to gain a better understanding of refunds, reimbursements, and replacements received.

Consistent with embodiments of the invention, a method for managing a returns process in response to product alerts is provided. The method includes receiving an alert related to a product. The method also includes processing the alert into an alert repository. The method further includes retrieving product data from a product repository based on the alert. The method further includes associating the product data with the alert. The method further includes facilitating a return of the product to a vendor using the product data. The method further includes receiving data in response to the return of the product. The method further includes providing an actionable display including the product data, the data in response to the return, and data related to a return action.

In another embodiment, a system for managing a returns process in response to product alerts is provided. The system includes an alert component. The alert component receives an alert related to a product. The alert component also processes the alert into an alert repository. The system also includes a return component. The return component retrieves product data based on the alert. The return component also associates the product data with the alert. The return component further facilitates a return of the product to a vendor using the product data. The return component further receives data in response to the return of the product. The returns module further provides an actionable display including the product data, the data in response to the return, and data related to a return action.

In yet another embodiment, a computer program product, tangibly embodied in computer-readable medium, is provided. The computer product is operable to cause data processing apparatus to receive an alert related to a product. The computer product is also operable to cause data processing apparatus to process the alert into an alert repository. The computer product is further operable to cause data processing apparatus to retrieve product data from a product repository based on the alert. The computer product is further operable to cause data processing apparatus to associate the product data with the alert. The computer product is further operable to cause data processing apparatus to facilitate a return of the product to a vendor using the product data. The computer product is further operable to cause data processing apparatus to receive data in response to the return of the product. The computer product is further operable to cause data processing apparatus to provide an actionable display including the product data, the data in response to the return, and data related to a return action.

It is to be understood that both the foregoing general description and the following detailed description are exemplary and explanatory only, and should not be considered restrictive of the scope of the invention, as claimed. Further features and/or variations may be provided in addition to those set forth herein. For example, embodiments consistent with the present invention may be directed to various combinations and subcombinations of the features described in the following detailed description.

BRIEF DESCRIPTION OF THE DRAWINGS

The accompanying drawings, which are incorporated in and constitute a part of this specification, illustrate various embodiments and aspects of the present invention. In the drawings:

FIGS. 5A-5C are screen displays of web pages generated and presented by an exemplary web application of an alert distribution and management system consistent with embodiments of the present invention;

FIG. 9A-9C are screen displays of web pages generated and presented by an exemplary web application incorporating a returns module consistent with embodiments of the present invention.

DESCRIPTION

Reference will now be made in detail to the invention, examples of which are illustrated in the accompanying drawings. Implementations set forth in the following description do not represent all implementations consistent with the claimed invention. Instead, they are merely some examples consistent with certain aspects related to the invention. Wherever possible, the same reference numbers will be used throughout the drawings to refer to the same or like parts.

Figure 1:
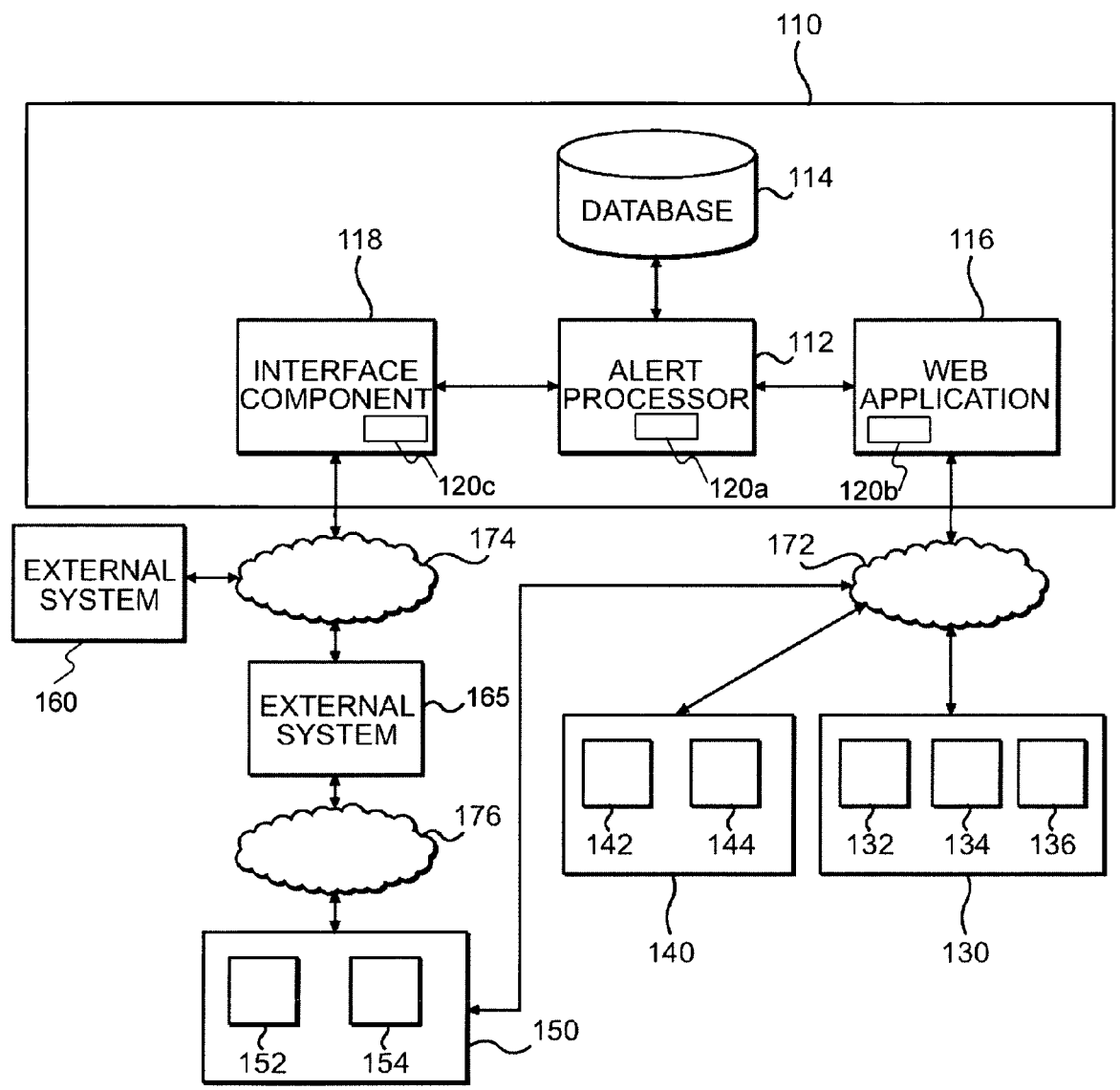
FIG. 1 is a block diagram illustrating an exemplary alert distribution and management system incorporating a returns module consistent with embodiments of the present invention.

FIG. 1 illustrates an exemplary alert distribution and management system 110 incorporating a returns module 120. In one embodiment, returns module 120 may include returns module part 120a, returns module part 120b, and returns module part 120c As shown in FIG. 1, system 110 may include alert processor 112, database 114, web application 116, and interface component 118. Alert processor 112, database 114, web application 116, and interface component 118 may include any number of computers, devices, hardware, and/or mainframe located anywhere and distributed among multiple locations. Alert processor 112, database 114, web application 116, and interface component 118 may also include operating systems, such as Microsoft Windows™, or any UNIX derived operating system, such as Linux®, Solaris™, and FreeBSD. In this embodiment, returns module 120 may have multiple parts 120a, 120b, and 120c distributed throughout system 110. For example, as shown in FIG. 1, part 120a may run as a part of alert processor 112, part 120b may run as a part of web application 116, and part 120c may run as a part of interface component 118. Although FIG. 1 shows that returns module 120 runs as a part of alert processor 112, web application 116, and interface component 118, returns module 120 may be separate from system 110, and may interact with system 110 seamlessly.

Alert processor 112 may perform alert distribution and management functionality, such as alert collection, distribution, management, and coordination assignment. For example, alert processor 112 may enable establishing accounts for new alert subscribing entities and enable obtaining, enhancing, and distributing alerts to alert subscribing entities. To this end, alert processor 112 may perform alert collection and distribution process 200 and alert management and coordination assignment process 300, as described in more detail with respect to FIGS. 2 and 3, respectively. Alert processor 112 may also include returns module part 120a. Returns module part 120a may perform processes related to management of returns, reimbursements, and replacements of alerted products.

Database 114 may include a database management system (DBMS). The DBMS may store and retrieve data from, and manage database 114. To this end, the DBMS may provide services such as transactions and concurrency, indexing, security, and backup and replication. The DBMS may be based on, for example, a relational model, object database model, post-relational database model, hierarchical model, or flat model. In certain embodiments, a DBMS may be implemented as Oracle™ DBMS, IBM's DB2™, Microsoft SQL Server™, PostgreSQL, or MySQL®.

Database 114 may also include a collection of data related to alert collection, distribution, management, and coordination assignment. For example, database 114 may store any data necessary for alert processor 112 to operate and provide its functionality. To this end, database 114 may include any data involved in alert collection and distribution process 200 and alert management and coordination assignment process 300, as described in more detail with respect to FIGS. 2 and 3, respectively. Database 114 may further include a collection of data related to management of returns, reimbursements, and replacements processes of alerted products.

Web application 116 may include a web server. The web server may accept hypertext transfer protocol (HTTP/HTTPS) requests from users, such as users 132, 134, 136, 142, 144, 152, and 154 through network 172, and send HTTP/HTTPS responses back to the users with web pages, which may comprise hypertext markup language (HTML) or extensible markup language (XML) documents and any linked or embedded objects, such as images. For example, the web server may exchange XML-based messages with the users using Simple Object Access Protocol (SOAP) on top of HTTP/HTTPS. In certain embodiments, the web server may be implemented as Apache HTTP Server™, Internet Information Service (IIS)™, Sun Java System Web Server™, or IBM HTTP Server™.

In certain embodiments, web application 116 may include an application server that enables dynamic generation of web pages. For example, web application 116 may employ Java Enterprise Edition (JEE) technologies, such as Java Server Page™ (JSP) and Java Servlet™, to enable dynamic generation of web pages, and a JEE application server, such as IBM's WebSphere™, BEA's WebLogic™, JBOSS™, and JRun™, may be implemented as an application server to support the technologies. Web application 116 may alternatively employ Microsoft .NET Framework™, such as ASP-.NET™ to enable dynamic generation of web pages.

Web application 116 may function as a user interface to alert processor 112 or of system 110, and expose the functionalities of alert processor 112 to users 132, 134, 136, 142, 144, 152, and/or 154. To this end, web application 116 may present web pages to the users, receive requests originated from the web pages by the users' actions, and repackage and/or relay the requests to alert processor 112 in the format understandable by alert processor 112. After alert processor 112 finishes processing the requests, web application 116 may receive results from the processing, generate web pages with the results, and present the web pages to the users. Web application 116 and exemplary web pages generated and presented by web application 116 are described in more detail with respect to FIGS. 5A-5C.

Web application 116 may include returns module part 120b. Returns module part 120b may function as a user interface to returns module part 120a, and expose the functionalities of returns module part 120a to users 132, 134, 136, 142, 144, 152, and/or 154. For example, users 132, 134, 136, 142, and 144 may manage returns, reimbursements, and replacements processes of alerted products using returns module part 120b as user interface. User commands or inputs received through returns module part 120b may be transmitted to returns module part 120a for processing and storage in database 114. Returns module part 120b and exemplary web pages generated and presented by returns module part 120b are described in more detail with respect to FIGS. 9A-9C.

Alert subscribing entities 130, 140, and 150 may subscribe to system 110 for alerts, and may access system 110 using web application 116, as shown in FIG. 1. Alert subscribing entities 130, 140, and 150 may also manage returns, reimbursement, and replacement processes of alerted products using returns module 120. Alert subscribing entities 130, 140, and 150 may be any organization that may receive, manage, and/or respond to alerts using system 110. For example, alert subscribing entities 130, 140, and 150 may be hospitals or medical centers that receive product recall alerts in areas such as biomedical devices, blood products, children's consumer product such as toys, food, laboratory products, medical supplies, pharmaceutical products, radiology products, tissues and organs, engineering and facilities related products and devices, and healthcare related hardware and software. In certain embodiments, alert subscribing entities 130, 140, and 150 may include a number of facilities, and each facility may receive alerts relevant to its functions only. For example, a facility with a pharmacy department may be interested in receiving product recall alerts in pharmaceutical products while a facility without a pharmacy department may not.

Alert subscribing entities 130, 140, and 150 may employ any number of users that may manage and respond to alerts. In certain embodiments, alert subscribing entity 130 may employ users 132, 134, and 136, alert subscribing entity 140 may employ users 142 and 144, alert subscribing entity 150 may employ users 152 and 154, as shown in FIG. 1. In certain embodiments, users 132, 134, and 136 may manage and respond to alerts for all facilities within alert subscribing entity 130 while users 142 and 144 may manage and respond to alert for only one facility within alert subscribing entity 140. In certain embodiments, users 132, 134, and 136 may be charged with a single role in managing and responding to alerts while users 142 and 144 may be charged with multiple roles in managing and responding to alerts. For example, user 142 may be charged with a managing role ("manager") that may require overseeing alert processing within alert subscribing entity 140. User 142 may also be charged with another role, such as an administrating role ("administrator") that may require handling administrative tasks, such as entering data into system 110.

User 134 may be charged with a coordinating role ("coordinator") that may require assigning alerts to a user charged with a responding role ("responder"). For example, in coordinating alerts, user 134 may assign a product recall alert to user 136, who may be a responder. The assignment may require user 136 to handle the alert by disposing of the recalled product. Failure to perform assigned roles may trigger an escalation process as described in greater detail with respect to FIG. 4. Actions that users 132, 134, 136, 142, 144, 152, and 154 may perform through web application 116 and returns module part 120b may be limited based on the assigned roles. In certain embodiments, however, any of users 132, 134, 136, 142, and 144 may access and perform any actions in returns module part 120b to manage returns, reimbursements, and replacements processes of the recalled products.

In certain embodiments where there may be multiple facilities within an alert subscribing entity, and a role may be further divided into multiple managing roles to account for the hierarchy within the entity. For example, a managing role within an alert subscribing entity may include an account manager and multiple facilities managers. An account manager may manage all alerts within the alert subscribing entity, and may be responsible for receiving daily summary of alert activities and workflow within the entity. Each facility within the entity may have a facility manager. A facility manager may manage all alerts within one facility, and may be responsible for receiving daily summary of alert activities and workflow within the facility only.

System 110 may interface with external systems 160 and 165 using interface component 118. In certain embodiments, external systems 160 and 165 may run outside the firewall of system 110, and connect to system 110 using one or more ports that are opened by interface component 118 for external systems 160 and 165. External systems 160 and 165 may be any system that interacts with system 110, for example, to request system 110 to perform a process or obtain data related to alert collection, distribution, management, coordination assignment, and returns, reimbursements, and replacements of alerted products. In certain embodiments, external systems 160 and 165 may receive a request from system 110. In response to the request, external systems 160 and 165 may perform a process and/or send data to system 110. Data from external systems 160 and 165, which may otherwise be entered manually into system 110, may be used in generating web pages of web application 116 including returns module part 120b although usage of the data is unlimited. In certain embodiments, external system 160 may be an enterprise resource planning (ERP) system, procurement system, accounting system, inventory system, materials management system, supply chain management system, and/or external database system.

Rather than using web application 116, alert subscribing entity 150 may alternatively receive, manage, and respond to subscribed alerts using external system 165. In certain embodiments, external system 165 may be any system that provides alert collection, distribution, management, and/or coordination assignment functionalities and/or alerted product returns, reimbursements, and replacements management functionalities but relies on alert processor 112 of system 110 for providing the functionalities. For example, external system 165 may retrieve alert data from system 110, and present the data to users 152 and 154. To this end, external system 165 may include its own user interface to present the retrieved data to users 152 and 154 and to interact with the users. Through its own user interface, external system 165 may customize the obtained alerts for its alert subscribing entities, such as entity 150. In certain embodiments, external system 165 may be developed or customized to provide alert management and coordination assignment services for a specific industry or a specific segment of an industry that may not conveniently use web application 116. By being external to system 110, external system 165 may receive user actions before they may reach system 110. In certain embodiments, external system 165 may modify and/or filter out the user actions in accordance with its own rules that may be more restrictive than ones implemented in system 110. The user interface of external system 165 may be implemented as a web-based application. To this end, external system 165 may include web servers, application servers, and/or databases.

As shown in FIG. 1, in some embodiments, interface component 118 may act as a gateway between external systems 160 and 165 and system 110. To support external systems developed under multiple technologies, interface component 118 may use a Service Oriented Architecture (SOA), and may be implemented using Common Object Request Broker Architecture (CORBA), Web Service, Simple Object Access Protocol (SOAP), Remote Procedure Call (RPC), Distributed Component Object Model (DCOM), or Windows Communication Foundation (WCF).

Networks 172, 174, and 176 may be any type of communication mechanism and may include, alone or in any suitable combination, a telephony-based network, a local area network (LAN), a wide area network (WAN), a dedicated intranet, wireless LAN, the Internet, an Intranet, a wireless network, a bus, or any other communication mechanisms. Further, any suitable combination of wired and/or wireless components and systems may provide networks 172, 174, and 176. Moreover, networks 172, 174, and 176 may be embodied using bidirectional, unidirectional, or dedicated communication links.

Figure 2:
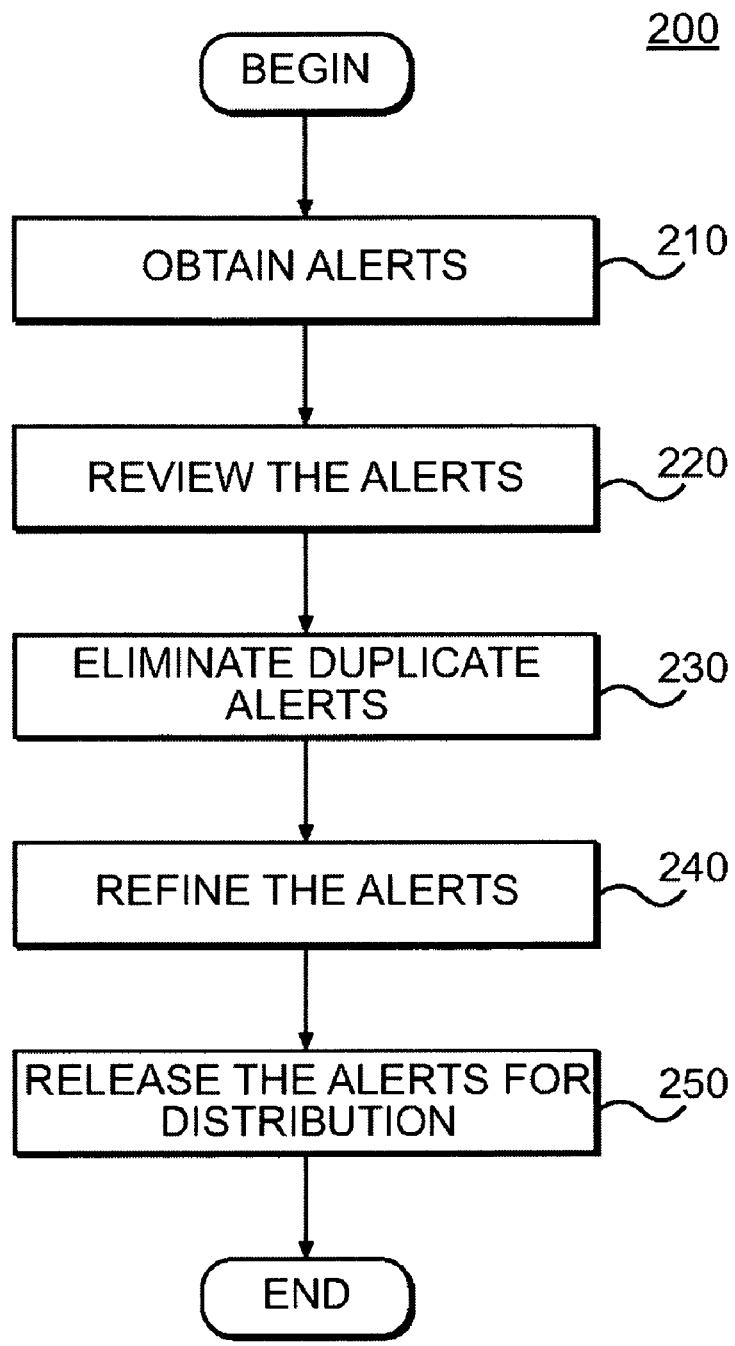
FIG. 2 is a flow diagram illustrating an exemplary alert collection and distribution process consistent with embodiments of the present invention.

FIG. 2 illustrates an exemplary alert collection and distribution process 200. System 110 may obtain alerts from multiple sources (step 210). For example, system 110 may obtain alerts from websites or other systems. System 110 may monitor the websites and other systems, and obtain alerts automatically when triggering events occurs. System 110 may also receive alerts from manufacturer recall notices. System 110 may further receive alerts from its alert subscribing entities, such as entities 130, 140, and 150. Once obtained, the alerts may be reviewed, for example, by a quality control staff, or automatic review process (step 220). Upon reviewing the alerts, the reviewer may delete duplicate alerts (step 230). System 110 may edit remaining alerts to enhance the quality of alert content (step 240). For example, system 110 may add additional information to clarify alerts. The alerts may then be put into a standard format with a consistent set of data elements, and released for distribution to alert subscribing entities (step 250). In certain embodiments, the released alerts may be filtered so that only desired alerts may reach each facility within the alert subscribing entities.

Figure 3:
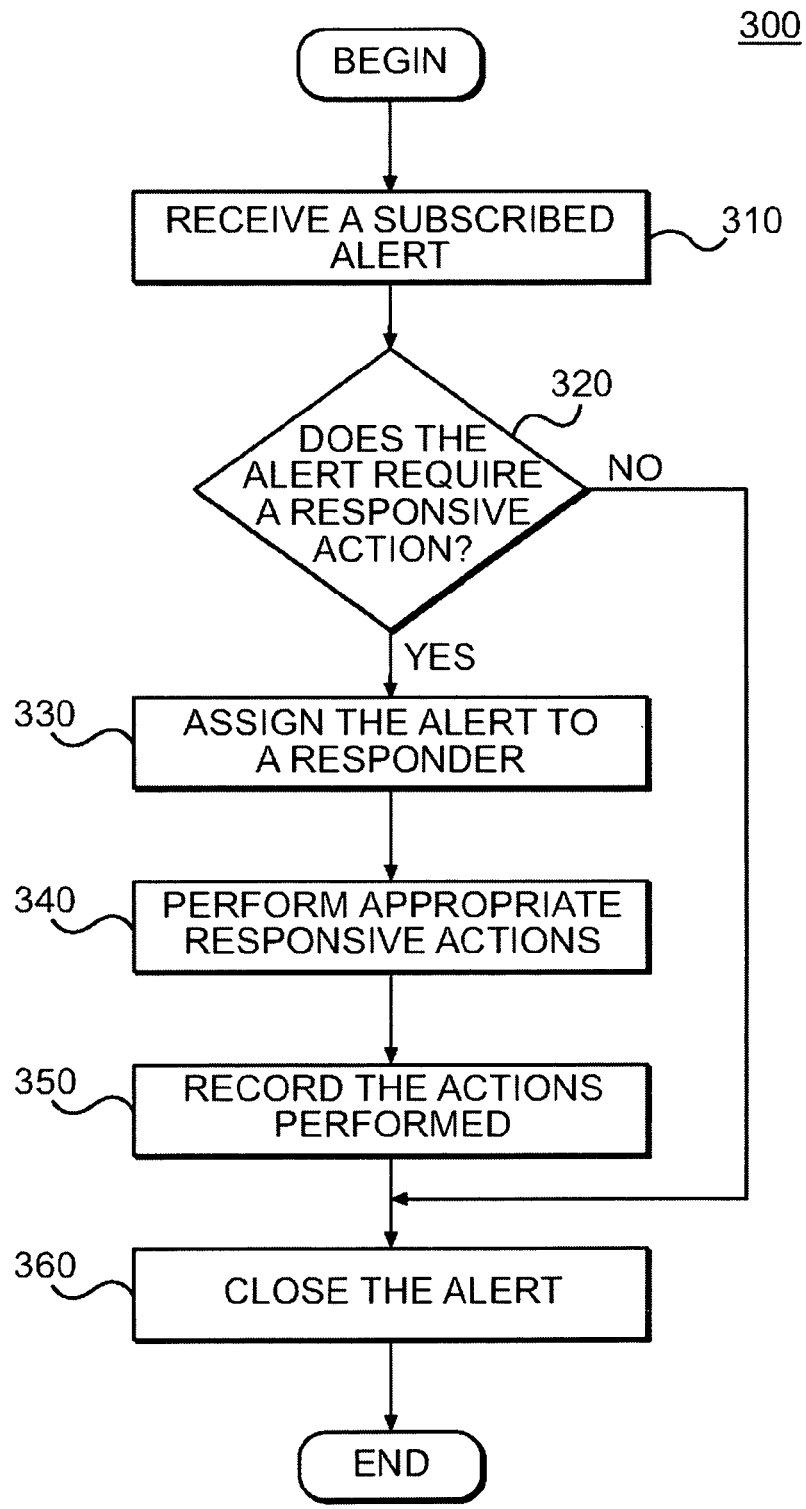
FIG. 3 is a flow diagram illustrating an exemplary alert management and coordination assignment process consistent with embodiments of the present invention.

FIG. 3 illustrates an exemplary alert management and coordination assignment process 300. Each facility within alert subscribing entities 130, 140, and 150 may receive a subscribed alert (step 310). A coordinator, such as user 134, may review the subscribed alert to determine whether it requires a responsive action (step 320). Upon review, if user 134 determines that the alert requires no further action (step 320 "No"), user 134 may close the alert (step 360). If user 134 determines that the alert requires a responsive action (step 320 "Yes"), user 134 may assign the alert to a responder, such as user 136 (step 330). User 136 may perform a task or tasks in response to the alert (step 340). For example, user 136 may dispose of any recalled products in response to a product recall alert. After user 136 completes the task(s), user 136 may record actions performed in system 110, e.g., by using web application 116 (step 350). User 134 may then close the alert (step 360). In certain embodiments, users may be notified by an e-mail at the completion of the step. For example, when a responder completes an action in response to an alert, a coordinator may receive an automatic e-mail notification via system 110.

Figure 4:
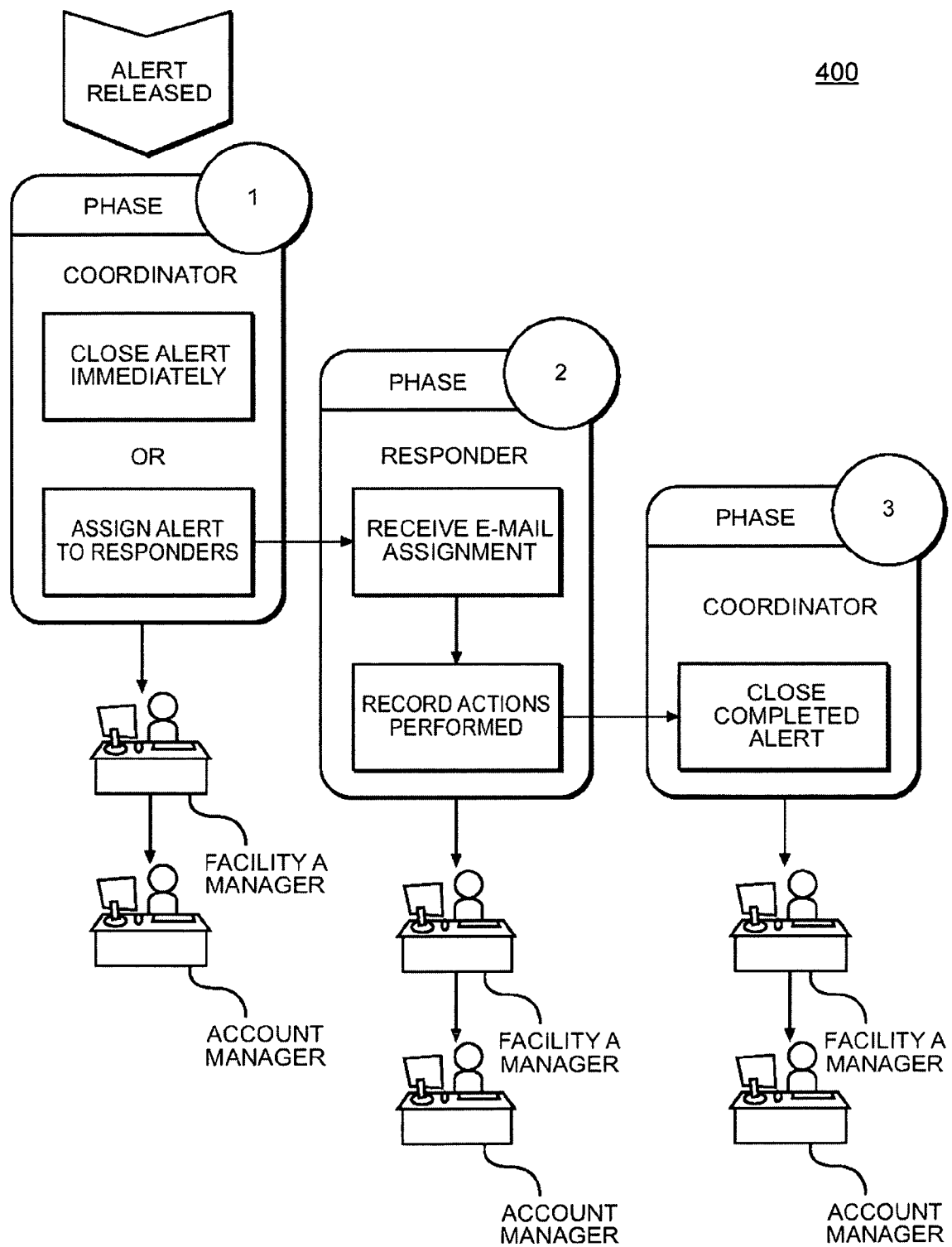
FIG. 4 is a block diagram illustrating an exemplary alert escalation process consistent with embodiments of the present invention.

FIG. 4 depicts an exemplary alert escalation process 400. As shown in FIG. 4, process 400 may comprise three phases. Phase 1 depicts a stage in alert management and coordination process 300 where an alert has been released to an alert subscribing entity. A coordinator who is assigned to the alert may have a specified number of days to take an action, for example by closing the alert or assigning the alert to a responder to handle the alert. In cases where the coordinator fails to take any action within the specified number of days, the alert may be escalated to a facility manager as shown in FIG. 4. The facility manager may have a specified number of days to take an action, for example, by reminding the coordinator of the alert or reassigning the alert to a different coordinator. If the facility manager fails to take an appropriate action within the specified number of days, the alert may be escalated to an account manager.

Phase 2 depicts a stage in alert management and coordination process 300 where the alert has been assigned to a responder. The responder has a specified number of days to take an action to handle the alert, for example, by disposing of alerted products and/or returning alerted products to a manufacturer, and record the actions performed. In cases where the responder fails to take an appropriate action within the specified number of days, the alert may be escalated to a facility manager as shown in FIG. 4. Similar to Phase 1, the facility manager may have a specified number of days to take an action. If the facility manager fails to take an appropriate action within the specified number of days, the alert may be escalated to an account manager.

Phase 3 depicts a stage in alert management and coordination process 300 where the alert has been handled by a responder and the action performed has been recorded. The coordinator who is assigned to the alert has a specified number of days to close the alert. In cases where the coordinator fails to close the alert within the specified number of days, the alert may be escalated to a facility manager as shown in FIG. 4. The facility manager may have a specified number of days to take an action. Failure to taken an action by the facility manager may escalate the alert to an account manager.

Figure 5A:
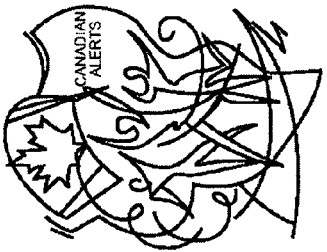
Figure 5C:
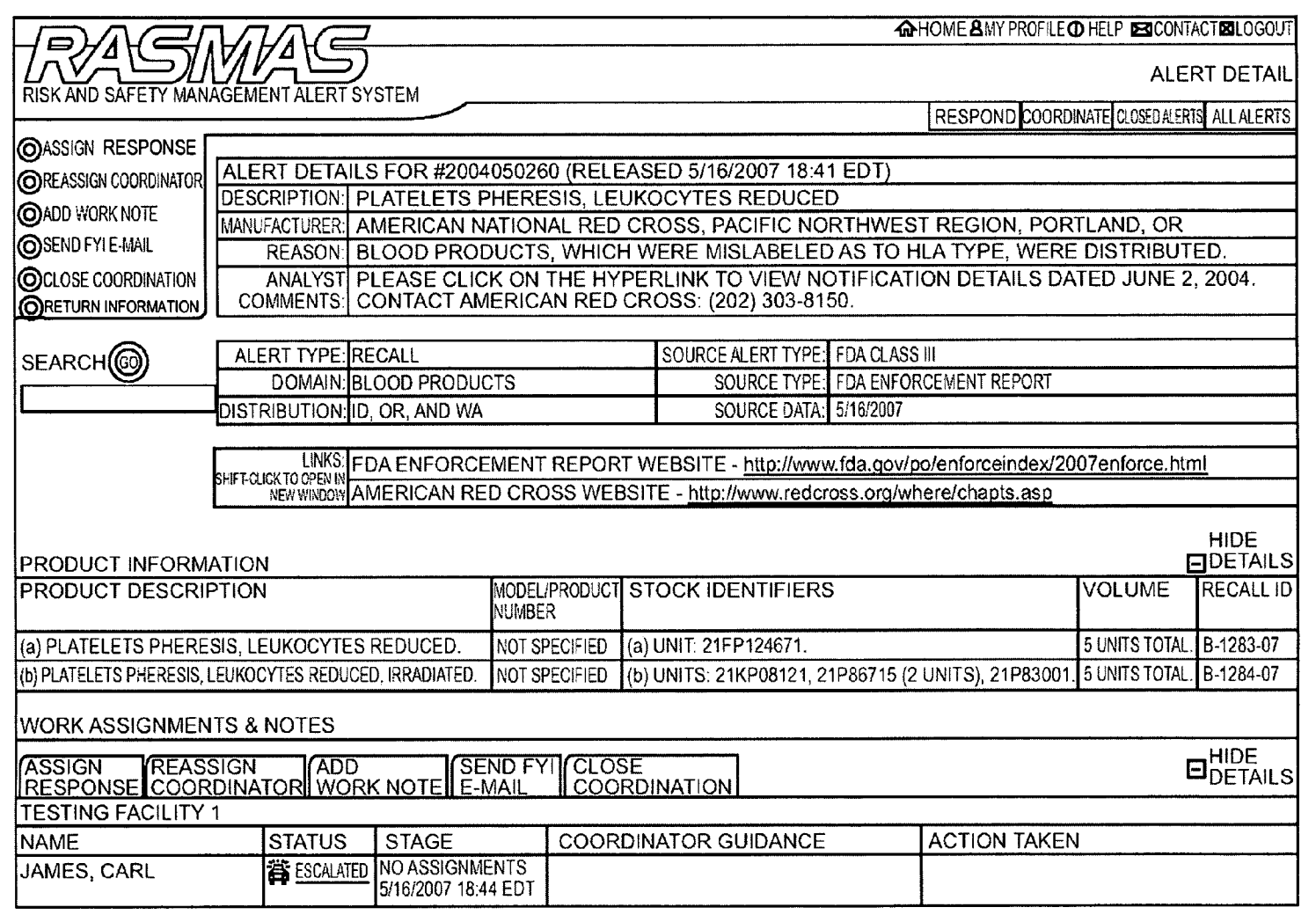

FIGS. 5A-5C depict screen displays of web pages generated and presented by exemplary web application 116 of system 110. A user may log into web application 116 and see a welcome screen, as shown in FIG. 5A. The left column of the welcome screen may display quick links, and the center column of the screen may display alert and recall related news or information. The right column of the screen may display a summary and status of currently open alerts that may require the user's action. For example, for the user "Carl Jones," an alert status shows that the user is a coordinator for five (5) alerts, with zero (0) alert as a responder or manager. As shown in the legend, colors or other indicators may show delayed or escalated alerts.

On the list screen shown in FIG. 5B, the user may see a list of the alerts that may require the user's action. The screen may include alert ID with alert release date, alert type, domain, description and manufacturer of the product being alerted, reason for alert, distribution of the alert, alert stage, and alert status. The user may take an action, such as closing the alert, on this screen.

On the detailed screen shown in FIG. 5C, the user may see more detailed information about one of the alerts listed on the list screen shown in FIG. 5B. The detailed information may include, in addition to the information shown in the list screen, comments by an alert analyst, source alert type, source type, detailed product information, and work assignments information. The detailed screen may include links to perform several actions, for example, in the left column as shown in FIG. 5C. In certain embodiments, the links may include "ASSIGN RESPONSE," "REASSIGN COORDINATOR," "ADD WORK NOTE," "SEND FYI E-MAIL," "CLOSE COORDINATION," and "RETURN INFORMATION" links. The "RETURN INFORMATION" link may direct the user to web pages generated and presented by returns module part 120b which are described in more detail with respect to FIGS. 9A-9C. Any screens of web application 116 may include a link to web pages generated and presented by returns module part 120b.

Figure 6:
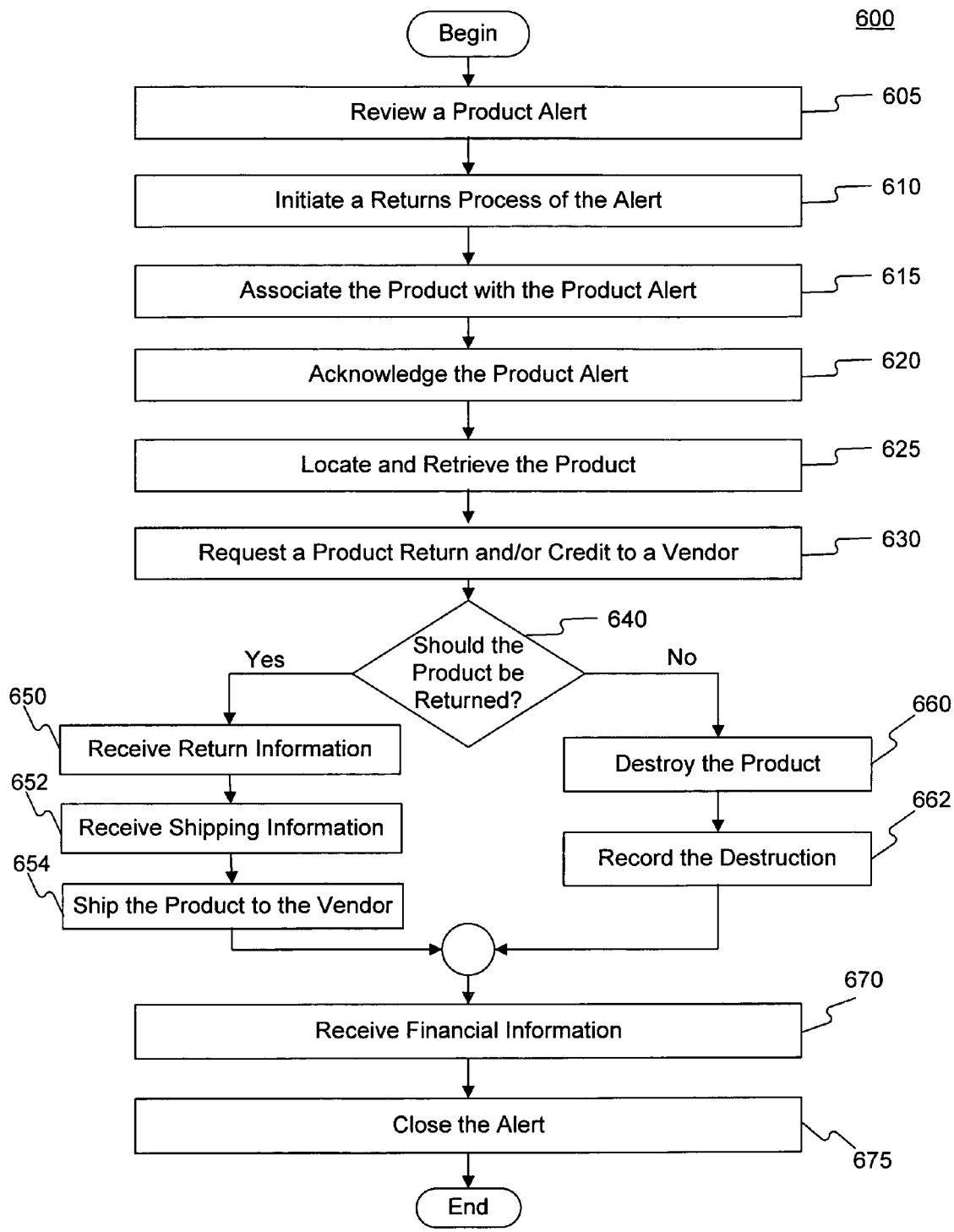
FIG. 6 is a flow diagram illustrating an exemplary returns process consistent with embodiments of the present invention.

FIG. 6 illustrates an exemplary returns process 600. An administrator may review a product alert, for example, by using web application 116 (step 605). The administrator may initiate a returns process in response to the alert (step 610). To this end, the administrator may retrieve purchasing history or inventory data of the alerted product(s) from a database and/or external system 160. The purchasing history and inventory data may include, among others, a product key, product description, model/product number, stock identifiers, facility stock identifiers, original volume, a vendor name or ID, a purchase order number, a number of the products in stock, and locations of the products. The administrator may associate the purchasing history and inventory data with the alert (step 615). To this end, the administrator may enter materials management advice into a returns module 120 based on the purchasing history and inventory data and other available data. The materials management advice may include a number of fields as described in more detail with respect to FIGS. 9B and 10. A coordinator may review the product alert and validate the materials management advice. A coordinator may enter additional advice into a returns module 120.

A responder may acknowledge the product alert (step 620), for example, by printing the product alert with a bar coded alert number. The responder may locate and retrieve the product (step 625). The responder may request a product return and/or credit from a vendor (step 630), for example, by completing a return requisition form. A vendor may be any entity involved in manufacturing and/or distribution of the product. Requesting a product return may further involve requesting a Return Material/Merchandise Authorization (RMA) number. The responder may also scan the product to indicate a product return. If it is determined that the product should be returned (step 640, "Yes"), return information may be entered into returns module 120 (step 650). In certain embodiments, returns module 120 may receive the return information from external system 160. When an RMA number is received from the vendor, shipping information may be entered into returns module 120 (step 652). In certain embodiments, returns module 120 may receive the shipping information from external system 160. The product may then be shipped to the vendor (step 654). If the responder determines that the product should not be returned (step 640 "No"), the responder may destroy the product (step 660). The responder may then record that the product has been destroyed (step 662), for example, by using returns module 120.

If a refund or credit for the product is received, financial information may be entered into returns module 120 (step 670). In certain embodiments, returns module 120 may receive the financial information from external system 160. The coordinator may verify the product alert, return, shipping, and/or financial information, and close the product alert (step 675). Although each step of process 600 is described to be performed by a specific role, any role may perform any step of process 600.

Figure 7:
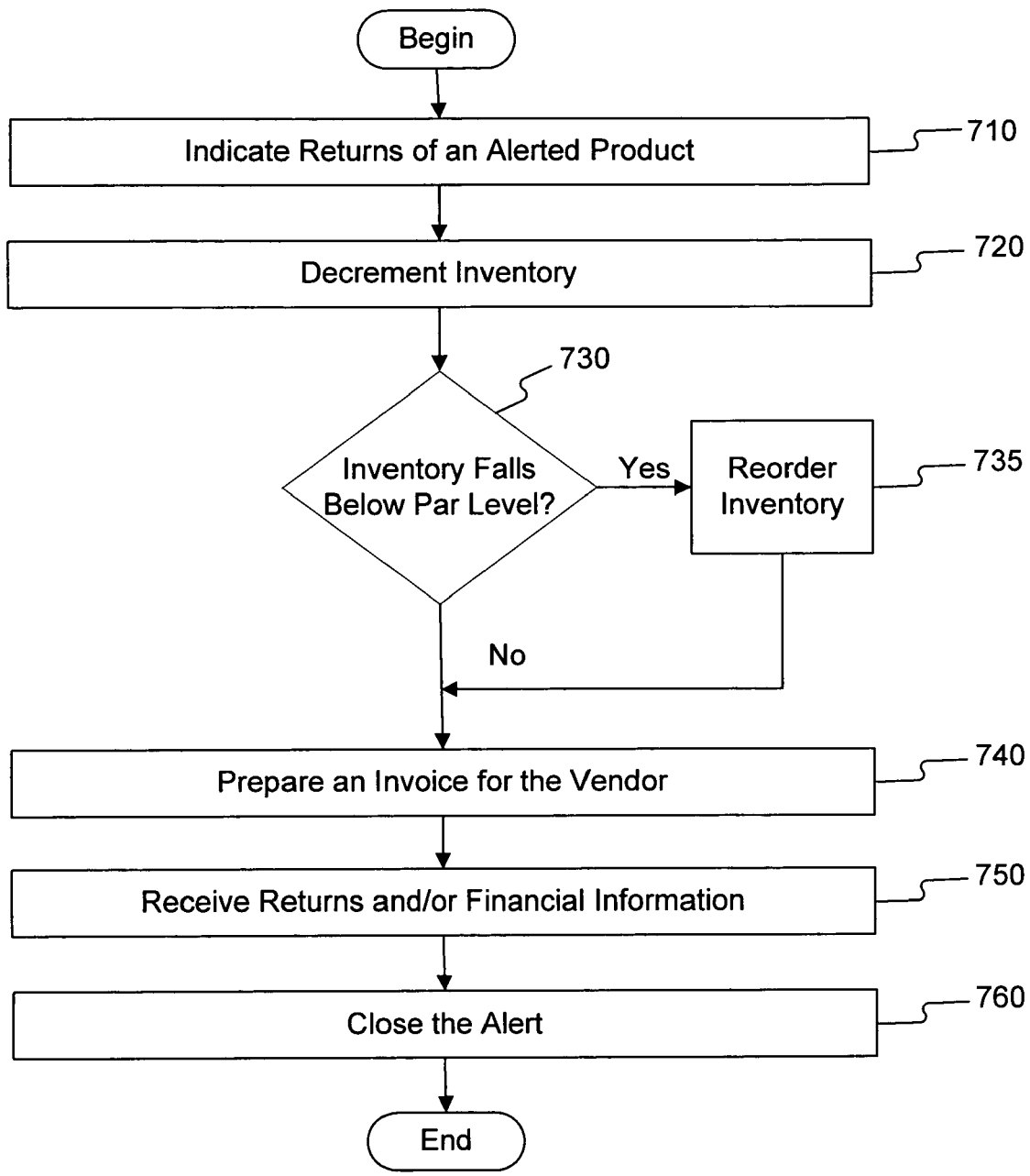
FIG. 7 is a flow diagram illustrating an exemplary replacements and reimbursements process consistent with embodiments of the present invention.

FIG. 7 illustrates an exemplary replacement and reimbursement process 700. While performing returns process 600, a responder may indicate a return of the alerted product (step 710), for example, by scanning the alerted product. The indication of return may decrement inventory by a number of the product (step 720). In certain embodiments, the indication of return may be notified to external system 160, and the external system 160 may update its inventory data. If the inventory falls below a par level after the decrement (step 730, "Yes"), the inventory may automatically be reordered (step 735). In certain embodiments, external system 160 may perform the step of reordering the inventory. An invoice may be prepared to receive reimbursement from the vendor (step 740). In certain embodiments, external system 160 may perform the step of preparing the invoice. Information related to the replacement and/or reimbursement may be entered into returns module 120. In certain embodiments, returns module 120 may receive the information from external system 160. A coordinator may verify the information and close the product alert (step 760).

Figure 8:
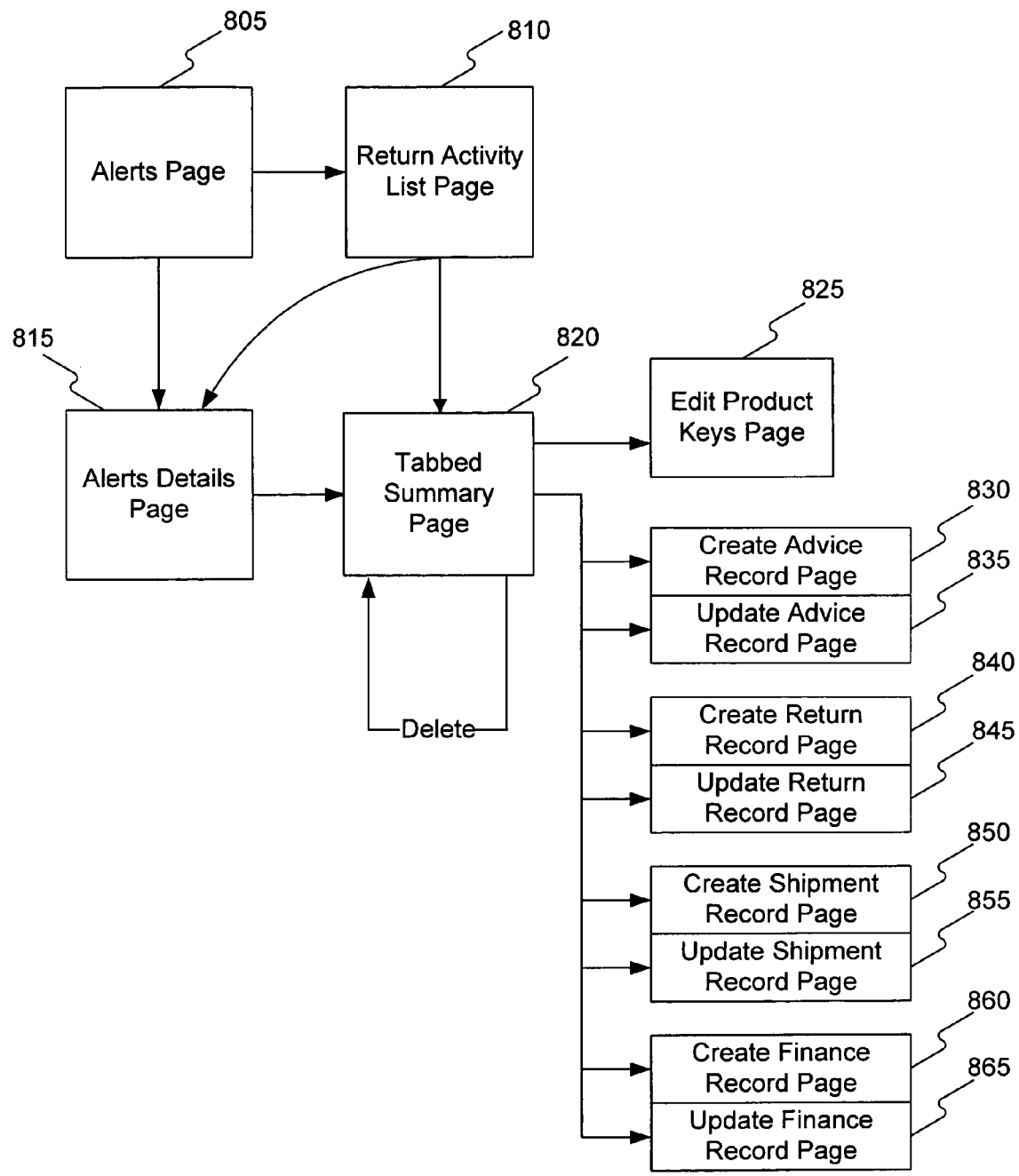
FIG. 8 is a block diagram illustrating exemplary page flows among web pages generated and presented by an exemplary web application incorporating a returns module consistent with embodiments of the present invention.

FIG. 8 illustrates exemplary page flows among exemplary web pages generated and presented by one embodiment of web application 116 incorporating returns module part 120b. Alerts page 805 may display a summary of alerts. From Alerts page 805, a user may be directed to Return Activity List page 810 or Alerts Details page 815 using a link displayed on page 805. Return Activity List page 810 may display a list of current return activities for the alerts. Alerts Details page 815 may display detailed information about one of the alerts. From Alerts List page 810, a user may be directed to Alerts Details page 815 or Tabbed Summary page 820. Tabbed Summary page 820 is described in more detail with respect to FIG. 9A. From Alerts Details page 815, a user may be directed to Tabbed Summary page 820.

Tabbed Summary page 820 may display detailed information about current return activities for the alerts. Tabbed Summary page 820 may provide a number of actions that a user may perform. If a user chooses to edit product keys on page 820, the user may be directed to Edit Product Keys page 825. If a user decides to create Advice, Return, Shipment, and Finance records, for example, from the materials management advice, return information, shipping information, and financial information received or collected during processes 600 and 700, the user may be directed to Create Advice Record page 830, Create Return Record page 840, Create Shipment Record, page 850, and Create Finance Record page 860, respectively. Create Advice Record page 830 and Create Finance Record page 860 are described in more detail with respect to FIGS. 9B and 9C, respectively. A user may edit the Advice, Return, Shipment, and Finance Records using Update Advice Record page 835, Update Return Record page 845, Update Shipment record page 855, and Update Finance Record, respectively. As shown in the embodiment of FIG. 8, a user may be directed to pages 835, 845, 855, and 865 from Tabbed Summary page 820.

Figure 9B:
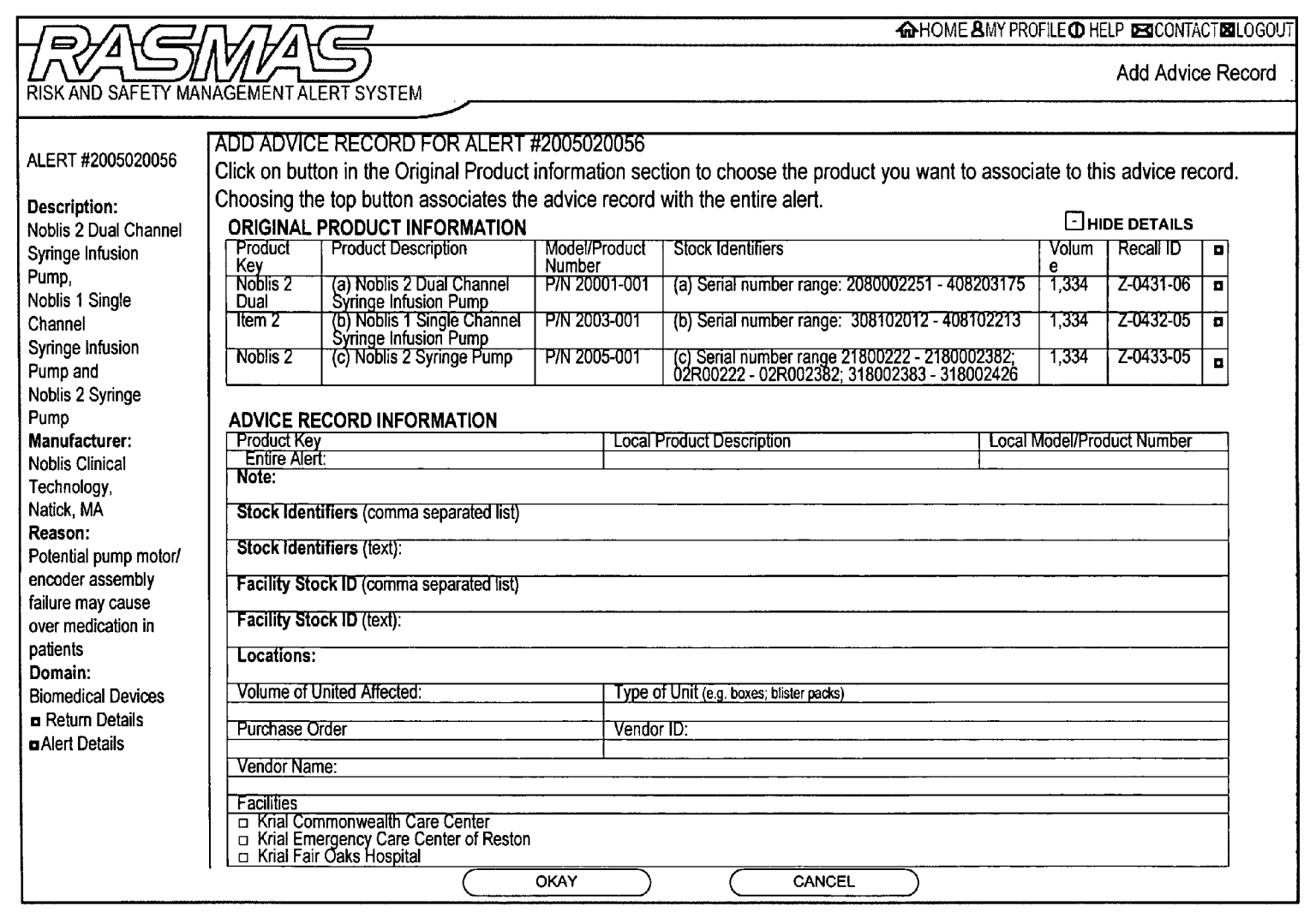

FIGS. 9A-9C depict screen displays of web pages generated and presented by exemplary web application 116 incorporating returns module part 120b. FIG. 9A depicts a screen display of Tabbed Summary page 820. The screen may display products that are affected by a specific alert. As shown in FIG. 9A, the screen displays three (3) products for Alert #2005020056. For each product, fields such as "Product Key," "Product Description," "Model/Product Number," "Stock Identifiers," "Volume," and "Recall ID" of the product may be displayed on the screen. The screen may include sorting and/or filtering mechanisms. As shown in FIG. 9A, the screen allows a user to sort and/or filter based on, for example, facilities, products, and/or activity creation dates. The screen may display more detailed information on returns activities for the products affected by the alert. The screen may use tabs to display more information in a limited area. As shown in FIG. 9A, the screen may include tabs such as "Advice," "Returns," "Procurement," "Financial," and "Summary" tabs.

When the "Advice" tab is selected, the screen may display the materials management advice received or collected during process 600. The materials management advice may be an instance of Advice class 1020, which is described in more detail with respect to FIG. 10. As shown in FIG. 9A, for each return activity, data such as "Product Key," "Note," "Location Description," "Stock Identifiers," "Facility Stock ID," "Locations," "Volume & Unit Type," "Purchase Order," and "Vendor ID/Name" may be displayed when the "Advice" tab is selected. When the "Returns" tab is selected, the screen may display the return information received or collected during processes 600 and/or 700. The return information may be represented as an instance of Return Data class 1030, which is described in more detail with respect to FIG. 10. To this end, any data fields from Base class 1010, and "ReturnDisposition" field may be displayed when the "Return" tab is selected.

When the "Procurement" tab is selected, the screen may display the shipping information received or collected during processes 600 and/or 700. The shipping information may be represented as an instance of Shipment class 1040, which is described in more detail with respect to FIG. 10. To this end, any data fields from Based class 1010, and "RMANumber,"
"VendorAuthorizingIndividual," "ReturnsAuthorizingIndividual," and "ReasonForCredit" fields may be displayed when the "Procurement" tab is selected. When the "Financial" tab is selected, the screen may display the financial information received or collected during processes 600 and/or 700. The financial information may be represented as an instance of Finances class 1050, which is described in more detail with respect to FIG. 10. To this end, any data fields from Base class 1010, and "Credit Taken," "CreditNumber," and "FinancialActivityType" fields may be displayed when the "Financial" tab is selected. When the "Summary" tab is selected, the screen may display a summary of the information on the returns activities. The materials management advice, returns information, shipping information, and financial information may be reported or presented to a user in any other form to provide a better understanding of returns processes and to enable user to manage returns, reimbursements, and replacements processes.

Tabbed Summary page 820 may provide a number of actions that a user may perform in managing returns, reimbursements, and replacements processes. For example, a user may delete a return activity from the page using "Delete" link as shown in FIG. 9A. A user may also edit an Advice, Return, Shipping, and Financial Record using "Edit" link as shown in FIG. 9A. In certain embodiments, a deleted record or prior record before update may be retained for audit. From Tabbed Summary page 820, a user may be directed to Edit Product Keys page 825 to edit a product key using the "Edit Product Key" tab. A user may also be directed to Create Advice Record page 830, Create Return Record page 840, Create Shipment Record page 850, and Create Finance Record page 860 using "Add Advice Record," "Add Return Record,", "Add Shipping Record," and "Add Financial Record" links, respectively.

FIG. 9B depicts a screen display of Create Advice Record page 830. The screen may display all products for which a new Advice Record may be created. As shown in FIG. 9B, the screen displays three (3) products for Alert #2005020056. For each product, data such as "Product Key," "Product Description," "Model/Product Number," "Stock Identifiers," "Volume," and "Recall ID" of the product may be displayed on the screen. A user may select a product for which a new Advice Record will be created. A user may then provide information, such as "Local Product Description," "Local Model/Product Number," "Note," "Stock Identifiers (comma separated list)," "Stock Identifier (text)," "Facility Stock ID (comma separated list)," "Facility Stock ID (text)," "Location," "Volume of Units Affected," "Types of Unit," "Purchase Order," "Vendor ID," "Vendor Name," and "Facilities" in the form provided on the screen. An administrator or coordinator may use the form on the screen to enter materials management advice into returns module 120 as described with respect to step 615 of process 600.

FIG. 9C depicts a screen display of Create Finance Record page 860. The screen may display all products for which a new Financial Record may be created. As shown in FIG. 9C, the screen displays three (3) products for Alert #2005020056. For each product, data such as "Product Key," "Product Description," "Model/Product Number," "Stock Identifiers," "Volume," and "Recall ID" of the product may be displayed on the screen. A user may select a product for which a new Financial Record will be created. A user may then provide information, such as "Local Product Description," "Local Model/Product Number," "Note," "Credit Taken," "Credit Number," "Financial Activity Type," and "Facilities" in the form provided on the screen. The form on the screen may be used to enter financial information as described with respect to step 670 of process 600 and step 750 of process 700.

Figure 10:
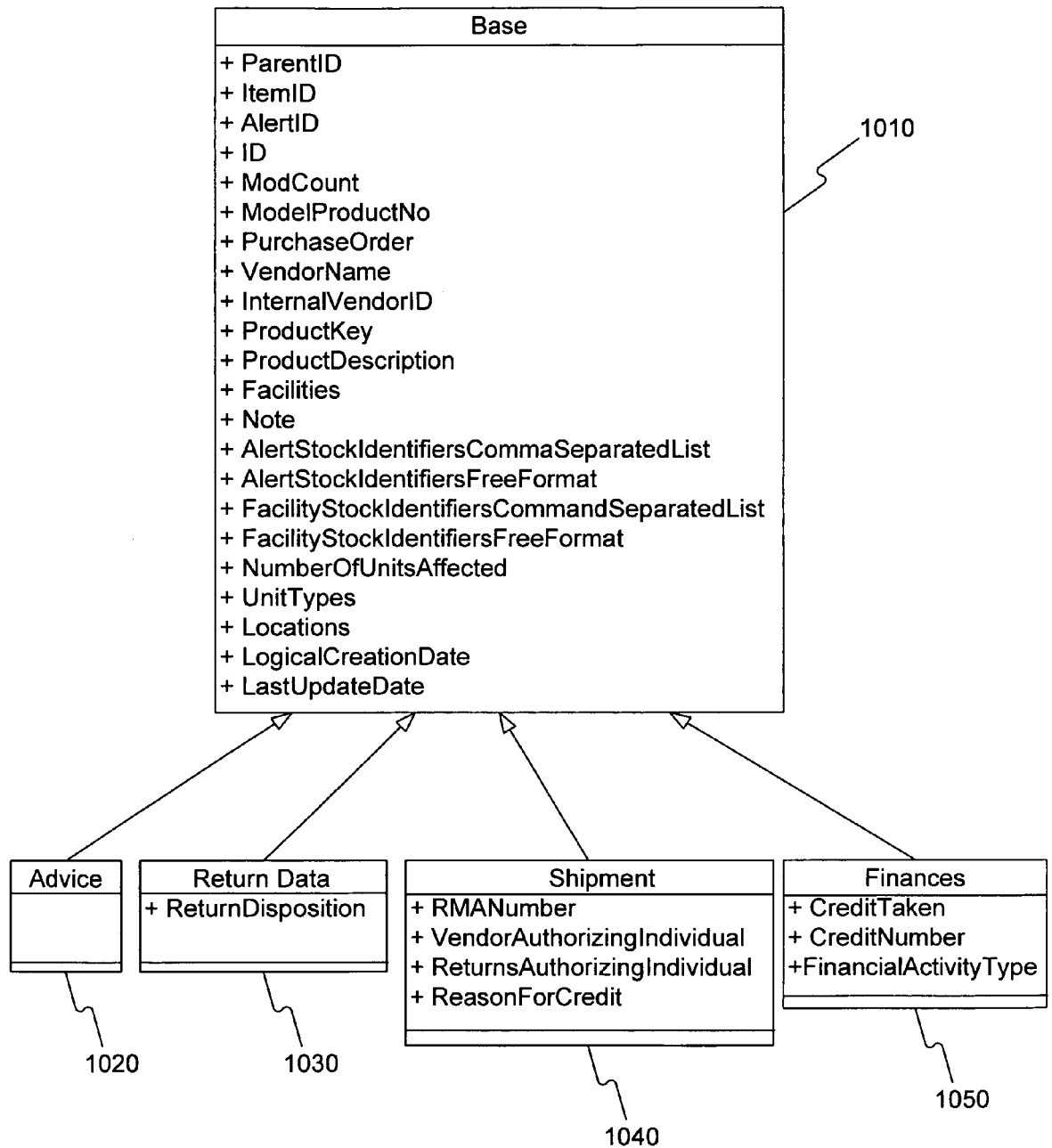
FIG. 10 is a class diagram of an exemplary returns module consistent with embodiments of the present invention.

FIG. 10 depicts a class diagram of exemplary classes available in returns module 120. Returns module 120 may include Base class 1010. Base class 1010 may include a number of data fields, such as "ParentID," "ItemID," "Alert ID," "ID," "ModCount," "ModelProductNo," "PurchaseOrder," "VendorName," "InternalVendorID," "ProductKey," "ProductDescription," "Facilities," "Note," "AlertStockIdentifiersCommaSeparatedList," "AlerStockIdentifiersFreeFormat," "FacilityStockIdentifiersCommaSeparatedList," "FacilityStockIdentifiersFreeFormat," "NumberOfUnitsAffected," "UnitTypes," "Locations," "LogicalCreation Date," and "LastUpdateDate" fields.

Subclasses, such as Advice class 1020, Return Data class 1030, Shipment class 1040, and Finances class 1050, may inherit the data fields of Base class 1010. The subclasses may include additional data fields. Advice class 1020 may include no additional data fields, and may have all the inherited data fields available. Advice class 1020 may be used to capture and hold the data received or collected using Create Advice Record page 830 and/or Update Advice Record page 835 during process 600.

Return Data class 1030 may include "ReturnDisposition" field. Return Data class 1030 may be used to capture and hold the data received or collected using Create Return Record page 840 and/or Update Return Record page 845 during processes 600 and 700. Shipment class 1040 may include "RMANumber," "VendorAuthorizingIndividual," "ReturnsAuthorizingIndividual," and "ReasonForCredit" fields. Shipment class 1040 may be used to capture and hold the data received or collected using Create Shipment Record page 850 and/or Update Shipment Record page 855 during processes 600 and 700. Finances class 1050 may include "CreditTaken," "CreditNumber," and "FinancialActivityType" fields. Finance class 1050 may be used to capture and hold the data received or collected using Create Finance Record page 860 and/or Update Finance Record page 865 during processes 600 and 700.

One of ordinary skill in the art will recognize that while the drawings illustrate the above steps in a particular order, the order in which the steps are carried out is irrelevant. Systems consistent with the invention may carry out the steps in any order or in some cases omit one or more steps without departing from the scope of the present disclosure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for managing a returns process in response to product alerts, the method comprising:

receiving, at a medical center, an alert related to a product at the medical center;

processing, by a processor at a web application, the alert into a database;

initiating, by the processor, a return of the product based on the alert;

receiving, by the processor, an alert handling advice related to the return of the product at the medical center;

facilitating, by the processor, the return of the product from the medical center to a vendor based on the alert handling advice;

updating, by the processor, an inventory of the product at the medical center to reflect the return of the product;

recording, by the processor, a responsive action taken at the medical center for the return of the product;

receiving, by the processor, financial information related to the return, by the medical center, of the product; and aggregating, using the processor, the financial information with the alert.

2. The method of claim 1, wherein initiating the return of the product further comprises retrieving product data for the product, the product data comprising the purchase history data and inventory data of the product currently in stock at the medical center.

3. The method of claim 2, wherein the purchase history data and the inventory data comprise one of a vendor name, a vendor ID, a purchase order number, a number of products in stock, a location of the products, and a stock identifier.

4. The method of claim 1, wherein facilitating the return of the product further comprises:

notifying the vendor of the return of the product related to the alert, and wherein updating the inventory of the product at the medical center to reflect the return of the product further comprises:

decrementing the inventory of the product at the medical center by a number of the product returned;

determining whether the inventory of the product at the medical center falls below a predetermined level; and automatically reordering the inventory of the product at the medical center upon a determination that the inventory falls below the predetermined level.

5. The method of claim 4, wherein notifying the vendor of the return of the product further comprises:

reporting the product to indicate the return of the product.

6. The method of claim 1, wherein facilitating the return of the product further comprises:

requesting the return of the product from the vendor; and requesting a credit from the vendor for the return.

7. The method of claim 6, wherein requesting the return further comprises:

requesting a return authorization number from the vendor.

8. The method of claim 1, wherein recording the responsive action taken at the medical center for the return of the product comprises recording return disposition information and shipment information, the return disposition information comprising what has been done with the product related to the alert, and the shipment information comprising a return authorization number from the vendor.

9. The method of claim 1, wherein the responsive action taken at the medical center for the return of the product further comprises requesting one of a refund, a reimbursement, and a replacement.

10. The method of claim 1, wherein the financial information related to the return of the product further comprises financial activity type, credit taken, and credit number.

11. A system for managing a returns process in response to product alerts, the system comprising:

a database; and a processor at a web application configured to:

process an alert that is related to a product and received by a medical center into the database;

initiate a return of the product based on the alert;

receive an alert handling advice related to the return of the product at the medical center;

facilitate the return of the product from the medical center to a vendor based on the alert handling advice;

update an inventory of the product at the medical center to reflect the return of the product;

record a responsive action taken at the medical center for the return of the product;

receive financial information related to the return, by the medical center, of the product; and aggregate the financial information with the alert.

12. The system of claim 11, wherein the processor is further configured to retrieve product data for the product, the product data comprising one of a vendor name, a vendor ID, a purchase order number, a number of products in stock, a location of the products, and a stock identifier.

13. The system of claim 11, wherein the processor is configured to facilitate the return of the product by:

notifying the vendor of the return of the product related to the alert, and wherein the processor is configured to update the inventory of the product at the medical center to reflect the return of the product by:

decrementing the inventory of the product at the medical center by a number of the product returned;

determining whether the inventory of the product at the medical center falls below a predetermined level; and automatically reordering the inventory of the product at the medical center upon a determination that the inventory falls below the predetermined level.

14. The system of claim 11, wherein the processor is configured to facilitate the return of the product by:

requesting the return of the product from the vendor; and requesting a credit from the vendor for the return.

15. The system of claim 11, wherein the processor is configured to record the responsive action taken at the medical center for the return of the product by recording return disposition information and shipment information, the return disposition information comprising what has been done with the product, and the shipment information comprising a return authorization number from the vendor, and wherein the responsive action taken at the medical center for the return of the product further comprises requesting one of a refund, a reimbursement, and a replacement.

16. The system of claim 15, wherein the financial information related to the return of the product further comprises financial activity type, credit taken, and credit number.

17. A computer program product, tangibly embodied in a computer-readable medium, the computer program product being operable to cause data processing apparatus at a web application to perform operations comprising:

processing an alert that is related to a product and received at a medical center into a database;

initiating a return of the product based on the alert;

receiving an alert handling advice related to the return of the product at the medical center;

facilitating the return of the product from the medical center to a vendor based on the alert handling advice;

updating an inventory of the product at the medical center to reflect the return of the product;

recording a responsive action taken at the medical center for receiving the return of the product;

receiving financial information related to the return, by the medical center, of the product, and aggregating, using the processor, the financial information with the alert.

18. The computer program product of claim 17, wherein initiating the return of the product further comprises retrieving product data, the product data comprising one of: a vendor name, a vendor ID, a purchase order number, a number of products in stock, a location of the products, and a stock identifier.

19. The computer program product of claim 17, wherein facilitating the return of the product further comprises:

notifying the vendor of the return of the product, and wherein updating the inventory of the product at the medical center to reflect the return of the product further comprises:

decrementing the inventory of the product at the medical center by a number of the product returned;

determining whether the inventory of the product at the medical center falls below a predetermined level; and automatically reordering the inventory of the product at the medical center upon a determination that the inventory falls below the predetermined level.

20. The computer program product of claim 17, wherein facilitating the return of the product further comprises:

requesting the return of the product from the vendor; and requesting a credit from the vendor for the return.

* * * * *